United States Patent [19]

Bahrmann et al.

[11] Patent Number: 5,369,162
[45] Date of Patent: Nov. 29, 1994

[54] DECYL ALCOHOL MIXTURES, PHTHALIC ESTERS OBTAINABLE THEREFROM AND THEIR USE AS PLASTICIZERS

[75] Inventors: Helmut Bahrmann, Hamminkeln; Wolfgang Greb; Peter Lappe, both of Dinslaken; Peter Heymanns, Essen; Jürgen Szameitat, Wessel; Thomas Müller, Dinslaken; Ernst Wiebus, Oberhausen, all of Germany

[73] Assignee: Hoechst Aktiengesellschaft, Germany

[21] Appl. No.: 85,551

[22] Filed: Jun. 30, 1993

Related U.S. Application Data

[62] Division of Ser. No. 34,267, Mar. 22, 1993, Pat. No. 5,268,514.

[30] Foreign Application Priority Data

Mar. 27, 1992 [DE] Germany ............... 4210026

[51] Int. Cl.$^5$ ................... C07C 69/76; C08K 5/09
[52] U.S. Cl. ...................... 524/296; 560/76
[58] Field of Search ............... 560/76; 524/296

[56] References Cited

U.S. PATENT DOCUMENTS

| | | | |
|---|---|---|---|
| 2,852,563 | 9/1958 | Hagemeyer et al. | 560/76 |
| 2,921,089 | 1/1960 | Hagemeyer et al. | 524/296 |
| 4,969,953 | 11/1990 | Miyazawa et al. | 560/76 |
| 5,268,514 | 12/1993 | Bahrmann et al. | 568/883 |

*Primary Examiner*—Joseph E. Evans
*Attorney, Agent, or Firm*—Jordan B. Bierman

[57] ABSTRACT

Mixtures of isomeric decyl alcohols are obtained by hydroformylation of 1-butene- and 2-butene-containing mixtures in two stages to give aldehyde mixtures, condensation of the isolated and combined aldehyde mixtures to form an aldol mixture, and isolation and hydrogenation of the aldol mixture. The mixture of isomeric decyl alcohols, esterified with phthalic acid, gives a mixture of isomeric decyl phthalates which are useful as plasticizers.

2 Claims, No Drawings

DECYL ALCOHOL MIXTURES, PHTHALIC ESTERS OBTAINABLE THEREFROM AND THEIR USE AS PLASTICIZERS

This application is a division, of application Ser. No. 08/034,267, filed Mar. 22, 1993, now U.S. Pat. No. 5,268,514.

This Application claims the priority of German Application P 42 10 026.7, filed Mar. 27, 1992.

The invention relates to mixtures of isomeric decyl alcohols, a process for the preparation thereof, the phthalic esters obtained from these alcohols, and their use as plasticizers.

BACKGROUND OF THE INVENTION

Esters of phthalic acid are used to a great extent as plasticizers, in particular for polyvinyl chloride. The principal alcohol components are primary alcohols having 8 to 10 carbon atoms; the most important of these is currently 2-ethylhexanol. Although phthalic esters of shorter-chain alcohols lead to plasticizers having good gelling capacity, their higher volatility is disadvantageous. Longer-chain esters, on the other hand, gel more slowly and have poorer cold resistance.

The properties of the phthalic ester plasticizers are influenced, not only by the size of the alcohol molecule, but also by the branching of the carbon chain. Thus, alcohols having little branching give ester plasticizers having high cold flexibility; substantially linear alcohols having 8 to 10 carbon atoms in the molecule are thus of increased importance as the alcohol components. A precondition for their use is that they are available in large amounts and at favorable cost.

According to German Patent 28 55 421, phthalates of nine carbon alcohols are used as plasticizers and are obtained by oxo reaction of eight carbon olefins, hydrogenation of the reaction product, and esterification of the resultant nine-carbon alcohols with phthalic anhydride. 3% to 20% by weight of the starting olefins have an isobutane skeleton in each molecule chain, less than 3% by weight of the olefins have quaternary carbon, and more than 90% by weight of the total amount of the olefins are present as n-octenes, monomethylheptenes, and dimethylhexenes. In addition, the weight ratio of the total amount of the n-octenes and monomethylheptenes to the dimethylhexenes is more than 0.8.

Phthalic esters based on ten-carbon alcohols are an object of European Patent Application 366,089. These alcohols are used in the form of a mixture which is obtained by hydroformylation of a butene fraction, aldol condensation of the resulting aldehyde mixture, and subsequent hydrogenation. The hydroformylation step is not subject to any restrictions, according to the process description. Thus, cobalt and/or rhodium can be used as catalysts, and the addition of an organic compound of trivalent phosphorus is not excluded.

Another route to obtain didecyl phthalate mixtures is described in European Patent Application 424,767. The preparation of the esters is carried out in a multi-stage process by dimerization of butene mixtures, hydroformylation and hydrogenation of the resulting octene mixture to give a nonanol mixture, dehydration of the nonanol mixture to form a nonene mixture, and hydroformylation and hydrogenation of the nonene mixture, thereby forming the desired decanol mixture.

From economic and industrial aspects, the known processes do not fulfill the requirements of a process carried out on an industrial scale. For example, the starting material may not be available in sufficient quantity, and/or may not be available at favorable costs, and/or the conversion of the starting materials into the alcohols may be associated with processes which are too expensive. In processes which start from butenes which are hydroformylated, the n-valeraldehyde content of the hydroformylation product should, in particular, be as high as possible, in order to promote the formation of straight- or only slightly branched-chain alcohols.

SUMMARY OF THE INVENTION

The object was, therefore, to develop a process which starts, not only from raw materials which are cheaply available, but also which can be converted in an industrially simple manner into the desired straight-chain or slightly branched chain alcohols.

The invention comprises mixtures of isomeric decyl alcohols which are obtained by hydroformylation of 1-butene- and 2-butene-containing mixtures in two stages. The reaction in the first stage is carried out, in a heterogeneous reaction system, in the presence of rhodium compounds containing complexed water-soluble phosphines as catalysts at temperatures of 70° to 150° C. and pressures of 0.4 to 30 MPa, thereby providing an aldehyde mixture. The second stage is effected in a homogeneous phase in the presence of rhodium compounds as catalysts at temperatures of 90° to 180° C. and pressures of 10 to 35 MPa also to give aldehyde mixtures. These mixtures are isolated from their reaction mixtures, combined, and condensed to form an aldol mixture. The aldol mixture is isolated and hydrogenated to give the desired mixture of isomeric decyl alcohols.

The 1-butene and 2-butene-containing mixtures used as starting materials for the inventive reaction are unavoidably produced in substantial amounts as refinery by-products in the production of automobile fuels and in the preparation of ethylene by thermal cracking of higher hydrocarbons. They are obtained from the four-carbon cracking cuts of the pyrolysis product. The butadiene is extracted by a selective solvent followed by isolation of the isobutene, preferably by conversion into methyl t-butyl ether. The pyrolysis product freed from butadiene is termed raffinate I; if, moreover, the isobutene is isolated, it is called raffinate II.

Instead of the butadiene being extracted, it can also be partially hydrogenated in the four-carbon cracking cut to give butenes. After isolation of the isobutenes, a 1-butene/2-butene mixture is obtained which is particularly suitable for further processing to decyl alcohols. Finally, there has recently been a move to hydrogenating the isolated butadiene to give butane, and returning it to the cracking process in order to increase the ethylene and propylene yield.

According to the invention, 1-butene- and 2-butene-containing mixtures, for example in the form of raffinate II (but also of other origin and composition), are hydroformylated in two stages. In the first stage 1-butene is preferably reacted to form a mixture which is predominantly n-valeraldehyde and, in a lesser amount, i-valeraldehyde. The reaction proceeds under conditions which substantially exclude isomerization of 1-butene to 2-butene. In the second stage, the 2-butene is hydroformylated to give a mixture of n-valeraldehyde and i-valeraldehyde.

DETAILED DESCRIPTION OF THE INVENTION

The first stage of the hydroformylation is carried out as a heterogeneous reaction in a two-phase system, a reaction which is described, for example, in German Patent 26 27 354. This process is characterized by the presence of an organic phase, which contains the starting olefins and the reaction product, and an aqueous phase, in which the catalyst is dissolved. Catalysts used are water-soluble rhodium complexes which contain water-soluble phosphines as ligands. The phosphines include, in particular, triarylphosphines, trialkylphosphines, and arylated or alkylated diphosphines. The organic radicals of the phosphines are substituted by sulfonic acid groups or carboxyl groups. Their preparation is taught, for example, in German Patent 26 27 354 and German Democratic Republic Patent 259 194.

The reaction of the butenes is carried out at temperatures of 70° to 150° C., preferably 100° to 130° C., and at pressures in the range of 0.4 to 30, in particular 1 to 10, MPa with water gas which contains carbon monoxide and hydrogen in the volume ratio 1:10 to 10:1. The rhodium concentration is 20 to 1000 ppm by weight, preferably 50 to 500 ppm by weight, based on the aqueous catalyst solution, and 4 to 100 mol of water-soluble phosphine are used per mole of rhodium. The volume ratio of aqueous to organic phase is 0.1 to 10:1.

The butene conversion is markedly increased if a phase transfer reagent (solubilizer) is added to the aqueous catalyst solution. Proven cationic solubilizers are of the formula $[A-N(R^1R^2R^3)]^+E^-$, in which A is a straight or branched-chain alkyl radical having 6 to 25 carbon atoms, $R^1$, $R^2$, $R^3$ are independently straight or branched-chain alkyl radicals having 1 to 4 carbon atoms; E may be sulfate, tetrafluoroborate, acetate, methosulfate, benzenesulfonate, alkylbenzenesulfonate, toluenesulfonate, lactate, or citrate. In the case of the conversion of 1-butene of up to 95%, depending on the reaction parameters selected, the aldehyde mixture contains 90% or more of n-valeraldehyde; the remainder is i-valeraldehyde.

Olefins (predominantly 2-butene) unreacted in the first stage, are hydroformylated in a second reaction stage in a homogeneous phase and in the presence of rhodium as a catalyst. Reaction temperatures which have been found suitable are 90° to 180° C., preferably 130° to 150° C., and pressures of 10 to 35 MPa, in particular 20 to 30 MPa. Rhodium is supplied to the reaction mixture as a metal, expediently in finely divided form or, preferably, as a compound soluble in organic media, for example a carbonyl compound or a salt of a carboxylic acid. The rhodium concentration is 2 to 100 ppm by weight, preferably 5 to 30 ppm by weight, based on the butenes introduced into the second reaction stage. The presence of a solvent such as toluene, xylene, or tetrahydrofuran, is not necessarily required, since its function can be taken over by the starting material and the reaction product. The water gas has the same composition as in the first reaction step. Depending on the reaction conditions, up to 99% of the olefin used is converted into n- and i-valeraldehyde.

After the hydroformylation is completed, the aldehyde mixtures of both reaction steps are isolated from the catalyst, from the unreacted reactants, and from the other reaction products. In the case of the heterogeneous reaction (first stage), this is achieved by simple phase separation. When the reaction takes place in homogeneous phase, i.e. in the second stage of the novel process, distillation is the conventional separation process.

The aldol condensation of the aldehydes present as a mixture is carried out by a conventional route in the presence of basic catalysts. A pretreatment of the aldehydes, for example a special purification, is not required. The catalysts used are alkali metal carbonates or alkali metal hydroxides, in particular compounds of sodium or potassium and amines, preferably tertiary amines, such as triethylamine, tri-n-propylamine, and tri-n-butylamine. Temperatures of 60° to 160° C. are employed, in particular 80° to 130° C., and the reaction is carried out under atmospheric pressure or elevated pressure up to about 1 MPa. The reaction time is from a few minutes to several hours and is dependent, in particular, on the type of catalyst and reaction temperature. Because of its higher reaction rate, n-valeraldehyde principally dimerizes with itself or with isomeric valeraldehydes to give decenals; in contrast, condensation of the branched five carbon aldehydes among themselves occurs completely in the background.

The aldehyde mixture obtained by condensation is then hydrogenated to give a decyl alcohol mixture. The hydrogen addition takes place in a known manner in the presence of catalysts. Suitable catalysts are, for example, hydrogenation catalysts based on nickel, chromium, or copper. The hydrogenation temperature is usually between 100° and 180° C., and the pressure between 1 and 10 MPa. The decyl alcohol mixture is distilled for purification. It is especially suitable as the alcohol component of phthalic esters which are to be used as plasticizers. The preparation of the phthalic esters is known (Ullmann, Encyclopädie der Technischen Chemie [Encyclopedia of Industrial Chemistry] (1979), volume 18, page 536 ff). Phthalic anhydride is expediently reacted with the decyl alcohol mixture in a molar ratio of 1:2 in a single stage. The reaction rate can be increased by catalysts and/or by increasing the reaction temperature. In order to displace the equilibrium in the direction of ester formation, it is necessary to eliminate the water formed from the reaction mixture.

The phthalates obtained from the decyl alcohol mixture according to the invention are plasticizers having excellent cold properties.

What we claim is:

1. A mixture of isomeric didecyl pthalates which is the reaction product of esterification of phthalic acid or phtalic anhydride with a mixture of isomeric decyl alcohols, said alcohols being a product of hydroformylation of a mixture consisting essentially of 1-butene and 2-butene in a first stage and further hydroformylating unreacted butenes from said first stage in a second stage, said first stage being carried out in a heterogenous reaction system in the presence of an aqueous solution of first rhodium compounds containing complexed water soluble phosphines as catalysts, said first stage taking place at a first reaction temperature of 20° to 150° C. and under a first reaction pressure of 0.1 to 20 MPa to form a first reaction mixture containing a first aldehyde mixture, said second stage being carried out in a homogenous phase in the presence of second rhodium compounds as catalysts, said second stage taking place at a second reaction temperature of 90° to 180° C. and under a second reaction pressure of 10 to 35 MPa to form a second reaction mixture containing a second aldehyde mixture, isolating said first aldehyde mixture from said first reaction mixture, isolating said second aldehyde mixture from said second reaction mixture, combining said first aldehyde mixture and said second aldehyde mixture to form a combined aldehyde mixture, condensing said combined mixture to form an aldol mixture, isolating and hydrogenating said aldol mixture to form said mixture of isomeric decyl alcohols.

2. A method of plasticizing a polymer comprising mixing therewith a mixture of isomeric didecyl phtalates of claim 1.

* * * * *